United States Patent [19]

Graham

[11] Patent Number: 4,542,176

[45] Date of Patent: Sep. 17, 1985

[54] PREPARATION OF PARTICULATE GELS

[75] Inventor: Neil B. Graham, Bearsden, Scotland

[73] Assignee: National Research Development Corporation, London, England

[21] Appl. No.: 667,403

[22] Filed: Nov. 5, 1984

Related U.S. Application Data

[63] Continuation of Ser. No. 387,775, Jun. 14, 1982, abandoned.

[30] Foreign Application Priority Data

Jun. 12, 1981 [GB] United Kingdom ............... 8118087

[51] Int. Cl.$^4$ ............................................. C08J 3/08
[52] U.S. Cl. ................................... 524/543; 524/548; 524/555; 524/556; 524/558; 524/591; 528/502
[58] Field of Search ............... 524/543, 548, 555, 556, 524/558, 591, ; 528/502

[56] References Cited

U.S. PATENT DOCUMENTS

| | | | |
|---|---|---|---|
| 2,427,513 | 9/1947 | Spessard | 523/322 |
| 2,658,045 | 11/1953 | Schildknecht | 524/548 |
| 3,245,934 | 4/1966 | Krzyszkowski | 523/322 |
| 3,864,432 | 2/1975 | Adler et al. | 523/322 |
| 3,867,281 | 2/1975 | Morgan et al. | 502/237 |
| 3,917,814 | 11/1975 | Hedges et al. | 424/23 |
| 3,963,685 | 6/1976 | Abrahams | 526/320 |
| 4,058,124 | 11/1977 | Yen et.al. | 524/543 |
| 4,069,161 | 1/1978 | Pogers | 528/502 |
| 4,109,070 | 8/1978 | Loshack et al. | 526/320 |
| 4,177,056 | 12/1979 | Mueller et al. | 71/93 |
| 4,192,827 | 3/1980 | Mueller et al. | 525/123 |
| 4,277,582 | 7/1981 | Mueller et al. | 525/404 |
| 4,304,591 | 12/1981 | Mueller et al. | 71/93 |
| 4,360,488 | 11/1982 | Barham et al. | 528/502 |
| 4,469,502 | 9/1984 | Heller et al. | 71/64.11 |

FOREIGN PATENT DOCUMENTS 1060764 3/1967 United Kingdom ............... 528/502

Primary Examiner—Joseph L. Schofer
Assistant Examiner—N. Sarofim
Attorney, Agent, or Firm—Oblon, Fisher, Spivak, McClelland & Maier

[57] ABSTRACT

A process for the preparation of a particulate gel, which process comprises (i) contacting the gel with a swelling agent and (ii) subjecting the swollen gel to shear stress such that the swollen gel is comminuted to particles.

11 Claims, 2 Drawing Figures

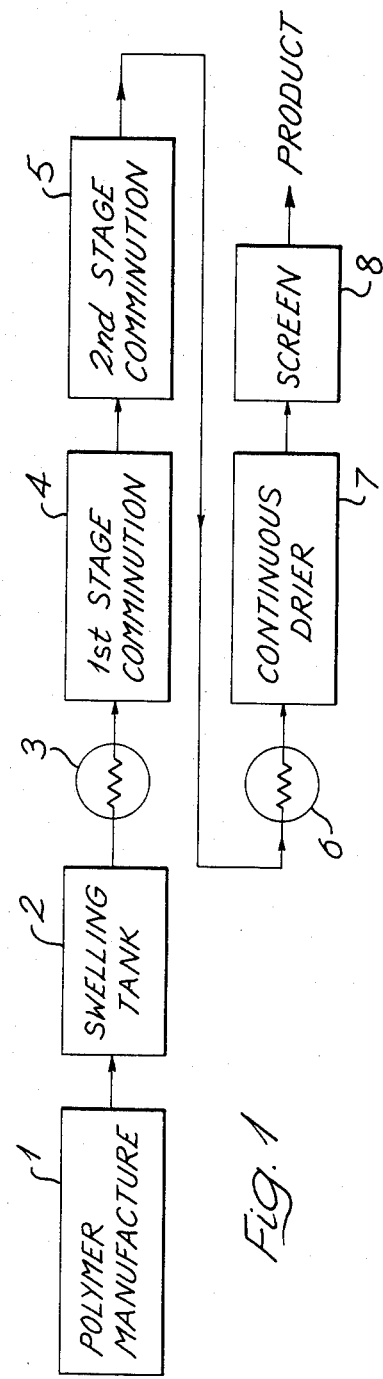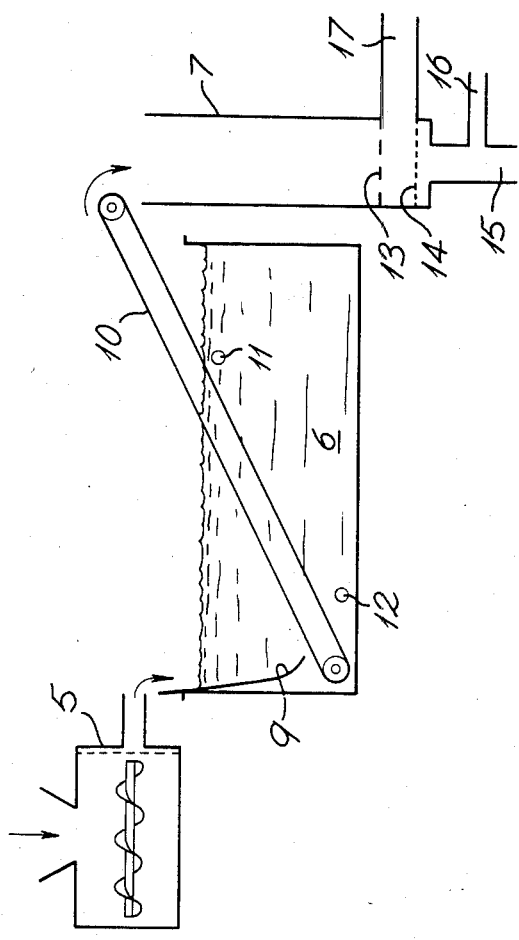

PREPARATION OF PARTICULATE GELS

This application is a continuation of application Ser. No. 387,775, filed June 14, 1982, now abandoned.

This invention relates to the preparation of gels, especially hydrogels, in particulate form.

In many applications to which gels are put it is more convenient that they be in particulate form. Conventionally, such particulate gels are prepared by an emulsion or suspension polymerisation process in which, however, there are separation and liquid handling problems. Bulk polymerisation processes, where such problems are either absent or diminished, result in the production of gels in more massive form.

According to the present invention, there is provided a process for the preparation of a particulate gel, which process comprises (i) contacting the gel with a swelling agent and (ii) subjecting the swollen gel to shear stress such that the swollen gel is comminuted to particles. By the term "gel" as used herein we mean a polymeric material which is swellable by, rather than soluble in, a given liquid. Usually, but not necessarily, the polymeric material may be rendered swellable by being chemically cross-linked. It may instead, either in the case of high molecular weight material, be trapped in an entanglement network, or be formed with hydrophobic blocks to give an amphipathic material.

In accordance with a particularly preferred feature of the invention the gel is a hydrogel and the swelling agent comprises water, optionally in admixture with one or more other polar liquids, for example $C_1$ to $C_4$ alkanols such as ethanol. From the standpoint of cheapness and availability, however, it is preferred that the hydrogel is swollen with a swelling agent which consists essentially of water, except where the hydrogel is readily hydrolysable in aqueous media. It is to be noted, however, that hydrogels can also be swollen by non-aqueous solvents, especially non-aqueous polar solvents: for example, chloroform.

Suitably, the hydrogel comprises a hydrophilic homo- or copolymer comprising residues derivable from at least one of the following monomer classes:

(a) (meth)acrylic acid, (meth)acrylamide or an unsubstituted or hydroxy-substituted ethyl or propyl (meth)acrylate, or a poly(oxyethylene) ester of (meth)acrylic acid;

(b) a substituted or unsubstituted cyclic mono or poly ether having from 3 to 6 ring atoms or cyclic imine having 3 ring atoms; or (c) a substituted or unsubstituted vinyl alcohol, aldehyde, ether, acetal, ketone, ester or substituted or unsubstituted N-vinyl heterocyclic compound.

By "(meth)acryl" we mean herein "methacryl" or "acryl" or a copolymer comprising both.

Monomers in class (b) include epoxides such as ethylene oxide, propylene oxide, 1,2-epoxybutane, 2,3-epoxybutane, glycidyl ethers, N-(epoxy substituted) heterocyclic compounds such as N-(2,3-epoxypropyl)-pyrrolidone; epihalohydrins, while not themselves cyclic ethers, do give homo- and copolymers derivable therefrom: examples include epifluorohydrin, epichlorohydrin and epibromohydrin. Other cyclic mono- or poly ethers include oxetane, tetrahydrofuran, dihydropyran, dioxolane and trioxane. Homo- and copolymers derivable therefrom include partially $C_1$ to $C_4$ alkyl etherified celluloses and starches, homo- and co-poly(alkylene oxides) which may be cross-linked through reaction with isocyanate or unsaturated cyclic ether groups such as polyoxymethylene, polyethylene glycols and polypropylene glycols, and polyesters thereof with dicarboxylate acids such as maleic acid.

Monomers in class (c) include methyl and ethyl vinyl ether, methyl vinyl ketone, methallyl alcohol, N-vinyl pyrrolidone, N-vinyl carbazole, N-vinyl pyridine, N-vinyl oxazole, N-vinyl methyloxazolidone, vinyl formal, vinyl butyral, vinyl methoxyacetal. Homo- and copolymers derivable therefrom include polyvinyl acetate and polyvinyl alcohol.

The process of this invention is particularly suited to homo- or copolymers which exhibit syneresis. Examples include homo- and co(polyethylene oxide) and the process of the present invention is particularly suited to poly(ethylene oxide). By the term "syneresis" as used herein we mean the spontaneous exudation of at least some of the swelling agent from the swollen gel which results when the temperature of the swollen gel is varied. In the case of homo- and co(polyethylene oxide) swollen with aqueous solvents and some non-aqueous solvents (for example formamide and acetic acid) syneresis occurs as the temperature is raised while for such polymers swollen with non-aqueous solvents syneresis in general occurs as the temperature is lowered.

It is found that the process of the present invention provides particulate gels of average particle size typically from 0.05 mm to 7 mm, preferably from 0.1 mm to 5 mm, of narrow particle size distribution substantially free from "fines", and that a very precise degree of control over the average particle size may be attained by appropriate regulation of one or more of the following parameters;

(a) the composition of the gel;
(b) the composition of the swelling agent;
(c) the temperature at which the swollen gel is subjected to shear stress;
(d) the rate of shear;
(e) the shear power;
(f) the nature and configuration of the shear means; and
(g) the duration of shear.

With regard to (a), the gel composition is usually dictated by the application to which the gel is put. However, a relative increase (in the case of a hydrogel copolymer) in the amount of a hydrophobic component or of chemical cross-linking, will reduce the amount of swelling caused by contact with an aqueous medium and, for a given set of parameters (b) to (g), will increase the average particle size of the sheared, swollen gel. The converse will also apply.

With regard to (b) the composition of the swelling agent will, for a given set of parameters (a) and (c) to (g), control the degree of swelling and the average particle size of the sheared, swollen gel. For example, a relative increase (in the case of a hydrogel polymer) in the amount of $C_3$ or $C_4$ alkanol in an aqueous swelling agent will decrease the amount of swelling and increase the average particle size of the sheared, swollen gel. However, by contrast an ethanol/water mixture approximating to 1:1 by weight composition will somewhat increase the amount of swelling, relative to water as the swelling agent, and decrease the average particle size of the sheared, swollen gel. Where (a) is such that the gel is sensitive to hydrolysis or alcoholysis, for example by being hydrolysable in aqueous media, then it may be swollen by any suitable non-aqueous swelling agent, for example chloroform. The gel may also be swollen with any suitable non-aqueous swelling agent and then sheared in aqueous media. Non-aqueous swelling agents can often provide greater swelling (for example, chloroform provides a ten-fold swelling relative to the dry weight, whereas water provides a four-fold swelling of poly(ethylene oxide) of equivalent weight about 3,500 at 37° C.) and thus a relatively smaller particle size after shearing and drying.

With regard to (c), where the swollen gel exhibits syneresis as the temperature is raised, in the case of homo- and co(polyethylene oxides) swollen in aqueous media, the regulation of the temperature at which the swollen gel is subjected to shear stress to effect syneresis will result in a less swollen gel and, for a given set of parameters (a), (b), (d), (e) and (f), will increase the average dried particle size of the sheared, swollen gel. The converse will also apply. This is a particularly preferred feature of this invention.

The shear may suitably be provided by an industrial mincer or blender, such as a Waring Blender; it is often convenient first to effect a coarse comminution followed by a fine comminution to specification.

Thereafter, the swollen particulate gel may be dried, optionally after impregnating with active substance which, where convenient, may be incorporated in the swelling agent.

In the case of gels, notably hydrogels comprising homo- and co-poly(ethylene oxide) swollen in aqueous media, which exhibit syneresis at elevated temperatures, an initial drying stage may comprise contacting the swollen, sheared gel with hot water, for example at a temperature from 90° to 100° C. The resulting syneresis will result in a reduction of the water content of the hydrogel the drying of which, if desired, can be completed after filtration by contact with a warm fluid current such as warm air.

In the case of gels, notably hydrogels comprising homo- and co-poly(ethylene oxide) having an equivalent weight greater than about 1,400 but swollen in non-aqueous media, which exhibit syneresis at reduced temperatures, an initial drying stage may comprise cooling the swollen, sheared gel, for example to a temperature from −25° C. to −25° C., preferably −20° C. to 0° C. whereupon the gel crystallises and the swelling agent is exuded.

The particulate gels, especially hydrogels, prepared by the process of this invention may be used in numerous applications. For example, they may be used as absorbents in diapers, tampons, incontinence pads and wound dressings; as gelling agents for containing aqueous media: for example, in bedpans or in incontinence bags where the aqueous medium is urine; as carriers, excipients and delivery mechanisms for active substances: for example, fertilisers, nutrients, herbicides, pesticides, flavourants and drugs, as described in our Specification Nos. 2047093, 2047094 and EP 0000291B1 and, in particular, in encapsulated controlled release orally-administered dosage forms; as soil conditioners; as humectants: for example in dried foods, tobacco, tea or coffee; and as extractive agents, as described in our Complete Specification No. 1573201.

In the specification accompanying our co-pending application No. 121959/121958/121640/2 we have described a hydrogel, suitable as a wound dressing agent and in the preparation of a controlled release composition comprising an active substance, which comprises polymerised moieties derivable from (i) at least one polymerisable cyclic(thio)ether and from (ii) at least one hydrophilic homo- or copolymer.

The process of this invention is particularly useful in preparing such hydrogels for use in such inventions.

In particular, the process of this invention, when practised on hydrogels comprising poly(ethylene oxide) moieties cross-linked through reaction with unsaturated cyclic ethers, such as acrolein tetramer, produces fine powders (with a mean diameter from 0.1 mm to 0.2 mm) very effectively with a short period of comminution in a Waring Blender.

In the case of hydrogels comprising poly(ethylene oxide) moieties cross-linked through reaction with isocyanates, such as an aliphatic diisocyanate, the effectiveness of comminution may be increased by foaming by the accidental or deliberate presence of a pneumatogen. This may comprise a small amount (typically less than 1% of reactants) of (i) water (which reacts in known manner with an isocyanate group to form carbon dioxide, the effective blowing agent, and an amine group which latter reacts with further isocyanate to form a urea group); (ii) an inert low boiling liquid (such as a halogenated, for example a chlorofluorinated hydrocarbon such as a freon); or (iii) a solid pneumatogen which decomposes on heating, for example a bicarbonate.

The process of the present invention is particularly advantageous in that the energy investment of comminution is low. The product is also formed in a particularly clean state for medical applications. In comparative tests, colourless unswollen hydrogel was comminuted by cryogenic grinding. A powder of broad particle size distribution was formed of grey or brown colour caused by metallic or other inclusions from the grinding mill. (Cryogenic grinding is also expensive.) The product produced by the process of this invention is a clear white powder of narrow particle size distribution which concomitant reduction in waste from material which is out of specification, or in energy investment in a classification process. The dried product, while free-flowing, does not impart slip to surfaces onto which it is poured, unlike certain presently available powders, comprising spherical particles. Furthermore, the swelling process enables free oligomeric and monomeric material to become extracted simultaneously.

On occasion, flocs of very fine (0.05 mm to 0.2 mm) particles can form on drying. This can be overcome by dry ball-milling.

The invention will now be further illustrated, by way of example, with reference to the accompanying drawing, in which:

FIG. 1 represents a diagrammatic flow-chart of the complete process; and

FIG. 2 represents a diagrammatic detailed view of a drying embodiment.

In the drawing, a poly(ethylene oxide) gel is manufactured by bulk polymerisation in reactor 1. The gel is conveyed to a swelling tank 2 where it is contacted in massive form overnight with water or a non-aqueous swelling agent becoming swollen thereby. The swollen gel together with excess water or non-aqueous swelling agent is then passed through a heat exchanger 3 in which it is brought to the particular temperature which will give the desired particle size after comminution in a coarse reduction stage 4 and a fine reduction stage 5. The comminuted slurry is next conveyed through a heat exchanger 6 in which it is heated to 100° C. or cooled to −25° C. to effect syneresis of water or non-aqueous swelling agent from the swollen gel. (The heat exchanger fluid exiting from 6 in the case where 6 is at 100° C. may be pumped in closed circuit to 3.) The less swollen gel leaving 6 is then dried to a free-flowing powder in a continuous drier 7 and next passed through a screening station 8 to give a comminuted product of specified particle size distribution.

In the particular embodiment shown in FIG. 2, the comminuted slurry leaving 5 is gravity fed by a guide 9 in 6 onto a moving endless belt 10. Water at 100° C. enters 6 at point 11 and cooler water leaves at point 12. The less swollen gel leaving 6 is then gravity fed into 7 where it meets a vibrating screen 13 of specified mesh size. Screened gel passes through to a static retaining mesh 14 while excess water is removed under tension through line 15. The screened gel is continually drained dry and next further dried by the passage of warm air through line 16. The dried gel is finally air veyed through line 17 to a fabricating station (not shown).

The following Examples illustrate the invention. In each case the gel was fully swollen before comminution. Gel particle sizes refer to the dry particle; mesh sizes refer to the mesh presented to the swollen polymer feedstock which is to be comminuted.

Gel particles were dried first by treating with boiling water for one minute on a vacuum filter on which they were then allowed to dry in air. Next they were fully dried using a through circulation air drier at 100° C.

Dried gel particles were sized using brass sieves in accordance with British Standard BS410/43.

EXAMPLE 1

A polyethylene oxide hydrogel cross-linked through urethane groups was first made by reacting poly(ethylene oxide) ($\overline{M}_n = 8307$) with 1,2,6-hexanetriol and Hylene W (bis-4'isocyanatocyclohexyl)methane) in the molar ratio 4:3:8.5 essentially as described in Example 1 of our specification 2047093A.

A swelling curve (which gives an indication of the extent of swelling and the time taken to attain this) for the hydrogel was then obtained by plotting water ratio against time at a constant ambient temperature of 20° C. (The water ratio is the ratio of the weight of water absorbed by the polymer at that temperature to the dry weight of polymer.) In the present case the equilibrium water ratio was found to be 3.5 and was attained after 6 hours (average of 3 samples).

Samples of the swollen hydrogel were next liquidised in a domestic liquidiser (Kenwood "Chef") for differing lengths of time but at constant liquidising shear (13,500 rpm) volume and weight ratio of polymer:ice:water (1:1:1). Groups of 5 samples were each liquidised for 1, 3, 5, 7 and 10 minutes making a total of 25 experimental runs: see Table 1. It was found that as the time of shear increased the percentage of sample weight remaining as coarse particles (that is, with a mean diameter greater than 1 mm) decreased with a concomitant increase in the amount of finer particles. It was also found that for shear times of 1 and 3 minutes the fraction which comprised the greatest percentage of sample weight was, in all cases, coarse; but that for a shear time of 5 and 7 minutes it was the fraction $<1003\mu$ but $>699\mu$ and for a shear time of 10 minutes it was the fraction $<699\mu$ but $>500\mu$.

These results indicate the desirability of increasing shear time to obtain increased amounts of finer particles.

EXAMPLE 2

Samples of swollen hydrogel, prepared as described in Example 1, were liquidised in the same liquidiser at different blade speeds but at constant liquidising times (1 min.), volume and weight ratio of polymer:ice:water (1:1:1). Groups of 5 samples were each liquidised at blade speeds of 4,000; 5,500; 8,000; 10,500 and 13,500, rpm making a total of 25 experimental runs: see Table 2. It was found that as the blade speed increased the percentage of sample weight remaining as coarse particles (that is, in this instance, with a mean diameter greater than 2.4 mm) decreased with a concomitant increase in the amount of finer particles. At the three highest blade speeds the fraction which comprised the greatest percentage (the percentage increasing with blade speed) of sample weight was, in each case, the fraction $<1405\mu$ but $>1003\mu$. At the highest blade speed this fraction comprised about 35% by weight of the sample and more than 50% by weight was under $2000\mu$.

These results indicate the desirability of increasing shear to obtain increased amounts of finer particles.

EXAMPLE 3

Samples of swollen hydrogel, prepared as described in Example 1, were liquidised in the same liquidiser at different weight ratios of polymer:ice:water but at constant liquidising time (10 minutes), shear (13,500 rpm) and volume. A sample was liquidised at each of the polymer:water:ice weight ratios 4:1:1, 3:1:1, 2:1:1 and 1:1:1 making a total of 4 experimental runs: see Table 3. It was found that as the ratio increased an optimum value, at about 3:1:1, was reached at which the percentage of sample weight converted to fine particles was greatest. The 3:1:1 sample gave approximately 60% by weight of the sample in the fraction $<600\mu$ but $>500\mu$ whereas the 4:1:1 sample gave approximately 60% by weight of the sample in the fraction $<1003\mu$ but $<599\mu$. The other two samples gave a high percentage of sample $>1003\mu$ with a poor yield of small particles.

These results indicate the desirability of using a high polymer:water:ice ratio but not one so high that the viscosity of the resulting mix reduces the shear (as was believed to be the case at 4:1:1).

EXAMPLE 4

Samples of swollen hydrogel of different volume, prepared as described in Example 1, were liquidised in the same liquidiser at constant liquidising times (10 minutes), shear (13,500 rpm) and weight ratio of polymer:ice:water (2:1:1) to ascertain whether any "scale-up" effect existed. Samples which had the volume of an equilibrated weight of polymer of 363, 487, 603 and 823 g, respectively, were each liquidised in a total of 4 experimental runs. It was found that as the volume of the sample increased the percentage of sample weight remaining as coarse particles (that is, with a mean diameter greater than 1 mm.) also increased. However, the corresponding decrease in the amount of finer particles at any given fraction was not great. For example, the fraction $<600\mu$ but $<500\mu$ comprised about 38%, 36%, 31% and 27% of the sample weight for the 363, 487, 603 and 823 g samples, respectively.

Accordingly, these results indicate that it may be more economical to use larger volume samples: while the percentage of sample weight yielded as fine particles will be smaller the actual weight of fine particles produced in unit time will be greater.

EXAMPLE 5

In this Example fractions from previous liquidising treatments, as feedstock, were extruded through a domestic mincer (Kenwood "Chef") modified by interposing a wire mesh between the supplied plates so as to obtain different mesh sizes. Results are shown in Table 5. These indicate that the several meshes did function to reduce a major amount of each feedstock below the mesh size; however, at small mesh sizes it appears that flocculation may occur. It is also possible that syneresis of the polymer occurs, due to heating, not only making it more difficult to comminute but also, thereafter, less able to dry down to the expected size.

EXAMPLE 6

A polyethylene oxide hydrogel crosslinked through reaction with unsaturated cyclic ether groups was made by reacting 550 g polyethylene glycol ($\overline{M}n=7000$) with 21.06 g 1,2,6-hexane triol and 126.68 g acrolein tetramer, 3,4-dihydro-2H pyran-2 methyl-(3,4-dihydro-2H pyran-2 carboxylate). The reactants differed from the stoichiometric molar ratio of 1:2:4 by the use of 80% excess of acrolein tetramer. The reaction was initiated by the addition of 0.7 g anhydrous ferric chloride, i.e. 0.1% by weight of the reactants.

The ferric chloride catalyst was dissolved in the triol at 90°; the dihydropyran and the moisture-free molten polyethylene glycol were then added and the reactants thoroughly mixed. The gel formed very rapidly and polymerisation was completed by curing for four hours at 90°.

The fully swollen gel was mixed with its own weight of water and liquidised in a domestic liquidiser (Kenwood Chef) for 10 minutes at 13,500 rpm. The gel particles were filtered off, treated with boiling water and then by through circulation warmed air.

The dried particles were sized by sieving to show a typical distribution of:

| Particle size (microns): | <420; | 420–500; | 500–699; | 699–1400; | >1400 |
|---|---|---|---|---|---|
| % by weight | 19; | 13; | 12; | 39; | 17 |

The particles were aggregated and could readily be reduced by further processing, for example light manual grinding with a mortar and pestle of particles larger than 420 microns reduced their size below this level.

The fine powder absorbs water very readily; 13.5 ml of water were absorbed by pouring from a measuring cylinder on to 3 g of the dry hydrogel, a water to dry powder ratio of 4.5.

EXAMPLE 7

A hydrogel was prepared as described in Example 1 using 67.8 g of polyethylene glycol ($\overline{M}n=7000$) 2.60 g of 1,2,6-hexane triol and 10.42 g of acrolein tetramer, i.e. 20% excess of the dihydropyran.

The hydrogel tended to disintegrate on swelling in water and readily comminuted with shearing. Thus, liquidising a 50,50 mixture of water and swollen gel for 20 minutes at maximum speed in a Kenwood Chef produced a frothy dispersion of very fine particles, estimated by optical microscopy to be in the 100 micron range. A slightly coarser dispersion made by liquidising at maximum speed for five minutes was filtered to give a filter cake of small discrete particles aggregated together to form a tough horn-like material.

TABLE 1

| TIME OF LIQUIDISING (MINS) | 1 | 3 | 5 | 7 | 10 | PARTICLE SIZES MESH NO | μ | WEIGHT PERCENTAGES 1 MIN SAMP. | 3 MIN SAMP. | 5 MIN SAMP. | 7 MIN SAMP. | 10 MIN SAMP. |
|---|---|---|---|---|---|---|---|---|---|---|---|---|
| weight of polymer/gms | 82.719 | 82.392 | 82.003 | 82.164 | 82.446 | rough | >1003 | 76.27 | 41.50 | 20.84 | 16.93 | 8.96 |
| weight of ice/gms | 81.857 | 81.858 | 82.039 | 82.284 | 81.027 | 16 mesh | <1003 but >699 | 18.60 | 43.32 | 43.12 | 50.83 | 36.84 |
| weight of water/gms | 83.463 | 82.573 | 82.679 | 82.107 | 82.181 | 22 mesh | <699 but >500 | 4.30 | 12.85 | 26.70 | 25.13 | 38.02 |
| weight of dried polymer/gms | 14.406 | 12.314 | 12.037 | 11.645 | 11.376 | 30 mesh | <500 but >422 | 0.46 | 1.28 | 4.40 | 3.40 | 6.94 |
|  |  |  |  |  |  | 36 mesh | <422 | 0.36 | 1.04 | 5.00 | 3.71 | 9.24 |

TABLE 2

| SPEED OF BLADES REV/MIN | 4000 | 5500 | 8000 | 10500 | 13500 | PARTICLE SIZES MESH NO | μ | WEIGHT PERCENTAGES 4000 rev/min | 5500 rev/min | 8000 rev/min | 10500 rev/min | 13500 rev/min |
|---|---|---|---|---|---|---|---|---|---|---|---|---|
| setting on control | 1 | 3 | 5 | 7 | MAX | rough | >2411 | 60.08 | 55.97 | 12.11 | 24.60 | 15.06 |
| wt. of polymer/gms | 82.104 | 81.740 | 82.172 | 82.774 | 82.013 | 7 mesh | <2411 but >1676 | 29.30 | 29.84 | 21.99 | 22.02 | 12.92 |
| wt. of ice/gms | 82.938 | 81.740 | 82.706 | 82.113 | 82.218 | 10 mesh | <1676 but >1405 | 5.72 | 6.99 | 23.30 | 18.49 | 19.69 |
| wt. of water/gms | 82.062 | 85.846 | 82.001 | 82.182 | 82.945 | 12 mesh | <1405 but >1003 | 3.79 | 5.87 | 30.72 | 25.42 | 34.54 |
| wt. of wet polymer/gms | 78.456 | 54.376 | 85.974 | 80.914 | 77.796 | 16 mesh | <1003 but >699 | 0.85 | 1.04 | 8.90 | 5.43 | 12.73 |
| wt. of hot water dried/gms | 63.597 | 43.266 | 50.640 | 65.214 | 65.292 | 22 mesh | <699 | 0.26 | 0.28 | 2.98 | 4.02 | 5.06 |
| % wt. loss due to H.W. | 18.94 | 16.75 | 41.10 | 19.40 | 16.07 |  |  |  |  |  |  |  |
| wt. of dry polymer/gms | 13.100 | 12.304 | 11.886 | 1.384 | 12.665 |  |  |  |  |  |  |  |

TABLE 3

| POLYMER:ICE:WATER RATIO | 1:1:1 | 2:1:1 | 3:1:1 | 4:1:1 | PARTICLE SIZES MESH NO | $\mu$ | WEIGHT PERCENTAGES 1:1:1 | 2:1:1 | 3:1:1 | 4:1:1 |
|---|---|---|---|---|---|---|---|---|---|---|
| wt. of polymer/gms | 59.433 | 119.413 | 179.693 | 239.964 | rough | >1003 | 23.19 | 15.38 | 0.52 | 0.55 |
| wt. of ice/gms | 59.436 | 59.098 | 60.541 | 60.838 | 16 mesh | <1003 but >699 | 43.52 | 29.98 | 6.09 | 30.92 |
| wt. of water/gms | 59.350 | 59.573 | 60.124 | 60.898 | 22 mesh | <699 but >599 | 15.47 | 21.85 | 30.66 | 31.09 |
| wt. of wet polymer/gms | 60.378 | 60.78 | 143.323 | 211.374 | 25 mesh | <599 but >500 | 8.76 | 15.50 | 30.76 | 19.24 |
| wt. of hot water dried/gms | 39.475 | 51.78 | 121.131 | 207.097 | 30 mesh | <500 but >422 | 3.93 | 7.10 | 17.14 | 8.29 |
| % wt. loss due to H.W. | 34.62 | 14.81 | 15.51 | 2.02 | 36 mesh | <422 but >251 | 4.69 | 9.11 | 13.88 | 9.28 |
| wt. of dry polymer/gms | 9.038 | 18.027 | 26.419 | 38.073 | 60 mesh | <251 but >211 | 0.22 | 0.57 | 0.49 | 0.33 |
| | | | | | 72 mesh | <211 but >178 | 0.17 | 0.35 | 0.35 | 0.22 |
| | | | | | 85 mesh | <178 | 0.05 | 0.16 | 0.11 | 0.09 |

TABLE 4

| TOTAL VOLUME/GMS | 362.991 | 486.935 | 603.232 | 822.626 | PARTICLE SIZES MESH NO | $\mu$ | WEIGHT PERCENTAGES 363 gms | 487 gms | 603 gms | 823 gms |
|---|---|---|---|---|---|---|---|---|---|---|
| wt. of polymer/gms | 180.551 | 240.782 | 302.274 | 399.955 | rough | >1003 | 4.94 | 4.90 | 7.73 | 4.85 |
| wt. of ice/gms | 91.992 | 119.832 | 149.691 | 222.175 | 16 mesh | <1003 but >699 | 11.43 | 17.84 | 30.30 | 43.22 |
| wt. of water/gms | 90.448 | 120.321 | 151.267 | 200.496 | 22 mesh | <699 but >599 | 38.38 | 35.54 | 31.29 | 27.39 |
| wt. of wet polymer/gms | 168.694 | 206.216 | 331.574 | 449.467 | 25 mesh | <599 but >500 | 21.57 | 21.06 | 16.48 | 13.21 |
| wt. of H.W. drying/gms | 116.464 | 143.158 | 263.163 | 374.417 | 30 mesh | <500 but >422 | 9.99 | 9.25 | 6.54 | 5.12 |
| % wt. loss due to H.W. | 30.96 | 30.58 | 20.51 | 16.70 | 36 mesh | <422 but >251 | 12.77 | 10.80 | 7.17 | 5.69 |
| wt. of dry polymer/gms | 27.332 | 34.214 | 51.434 | 63.408 | 60 mesh | <251 but >211 | 0.56 | 0.41 | 0.23 | 0.25 |
| | | | | | 72 mesh | <211 | 0.36 | 0.34 | 0.27 | 0.25 |

TABLE 5

| SAMPLE | FEEDSTOCK FRACTION | MESH | PRODUCT MODE PTCLE. SIZE | THROUGHPUT (g min$^{-1}$ cm$^{-2}$) | PERCENTAGE (BEST) BY WEIGHT FEEDSTOCK NOT EXCEEDING MODE PTCLE. SIZE |
|---|---|---|---|---|---|
| 1 | >1000$\mu$ | 910$\mu$ | 600$\mu$ | 1.806 | 50 |
| 2 | <1000$\mu$ but >700$\mu$ | 910$\mu$ | 600$\mu$ | 3.671 | |
| 3 | <750$\mu$ but >450$\mu$ | 910 | 600$\mu$ | 3.970 | |
| 4 | >1000$\mu$ | 580$\mu$ | 422$\mu$ | 0.883 | 60 |
| 5 | <1000$\mu$ but >700$\mu$ | 580$\mu$ | 422$\mu$ | 2.078 | |
| 6 | <750$\mu$ but >450$\mu$ | 580$\mu$ | 422$\mu$ | 1.542 | |
| 7 | >1000$\mu$ | 320$\mu$ | 400*$\mu$ | 0.155 | <50 |
| 8 | <1000$\mu$ but >700$\mu$ | 320$\mu$ | 400$\mu$ | 0.168 | |
| 9 | <750$\mu$ but >450$\mu$ | 320$\mu$ | 400$\mu$ | 0.137 | |
| 10 | >1000$\mu$ | 180$\mu$ | 124$\mu$ | 0.011 | <50 |
| 11 | <1000$\mu$ but >700$\mu$ | 180$\mu$ | 124$\mu$ | 0.018 | |
| 12 | <750$\mu$ but >450$\mu$ | 180$\mu$ | 124$\mu$ | 0.016 | |

*believed due to flocculation

I claim:

1. A process for the preparation of a particulate hydrogel of a homo-or copolymer which can exhibit syneresis, which process comprises:
   (i) contacting the hydrogel with a swelling agent;
   (ii) subjecting the swollen hydrogel to shear stress such that the swollen hydrogel is comminuted to particles; and
   (iii) drying the swollen particulate hydrogel by varying its temperature so that it exhibits syneresis.

2. The process according to claim 1, wherein the swelling agent comprises water.

3. The process according to claim 2 wherein the swelling agent consists essentially of water.

4. The process according to claim 2 or 3, wherein the hydrogel comprises a hydrophilic homo- or copolymer comprising residues derivable from at least one of the following monomer classes:
   (a) (meth)acrylic acid, (meth)acrylamide or an unsubstituted or hydroxy-substituted ethyl or propyl (meth)acrylate, or a poly(oxyethylene) ester of (meth)acrylic acid;
   (b) a substituted or unsubstituted cyclic mono or polyether having from 3 to 6 ring atoms; or
   (c) a substituted or unsubstituted vinyl alcohol, aldehyde, ether, acetal, ketone, ester or substituted or unsubstituted N-vinyl heterocyclic compound.

5. A particulate gel prepared in accordance with the process of claim 1, 2 or 3.

6. The particulate gel according to claim 5 which comprises an active substance.

7. The process according to claim 2, 3 or 1, wherein the hydrogel comprises a homo-or copoly(alkylene)oxide.

8. The process according to claim 7, wherein the poly(alkylene oxide) is cross-linked through reaction with isocyanate or unsaturated cyclic ether groups.

9. The process according to claim 2, 3, or 1, wherein the hydrogel comprises a poly(ethylene oxide).

10. The process according to claim 2, 3 or 1, wherein the temperature at which the swollen gel is subjected to shear stress is regulated to provide a desired average particle size.

11. The process according to claim 2, 3 or 1, wherein an active substance is incorporated in the swelling agent.

* * * * *